United States Patent [19]

Dean

[11] Patent Number: 4,980,148
[45] Date of Patent: Dec. 25, 1990

[54] METHODS FOR ENHANCING MAGNETIC RESONANCE IMAGING

[75] Inventor: Richard T. Dean, Chesterfield, Mo.

[73] Assignee: Mallinckrodt, Inc., St. Louis, Minn.

[21] Appl. No.: 698,895

[22] Filed: Feb. 6, 1985

[51] Int. Cl.$^5$ ............................................. A61K 49/00
[52] U.S. Cl. .................................... 424/9; 128/653 A; 128/654; 534/13
[58] Field of Search ...................... 260/479 J; 224/309; 128/653, 654; 424/9; 534/13

[56] References Cited

U.S. PATENT DOCUMENTS 4,472,509  9/1984  Ganson et al. ................... 436/819 X
4,647,447  3/1987  Gries et al. .............................. 424/9

FOREIGN PATENT DOCUMENTS 2137612  10/1984  United Kingdom .

OTHER PUBLICATIONS

Runge et al., AJR, vol. 141, (1983), pp. 1209–1215.
Martell et al., Chemistry of the Metal Chelate Compounds, Prentice–Hall, Inc., (1952), pp. 181–183.
Sigma, Biochemical and Organic Compounds, Price List, Feb. 1982, p. 306, E4378.
Chemical Abstracts, vol. 98, no. 1, (1983), 98:3795x.

Primary Examiner—Richard L. Raymond
Attorney, Agent, or Firm—Senniger, Powers, Leavitt & Roedel

[57] ABSTRACT

Substantially nontoxic manganese or gadolinium complexes of compounds of the formula:

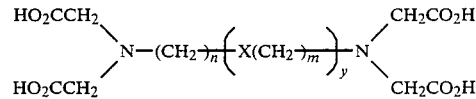

wherein n and m=1, 2, 3 or 4, y=1, 2 or 3, and x is selected from the group consisting of O, S, CHOH and CHSH, are useful for enhancing magnetic resonance images of body organs and tissues. Illustrative manganese and gadolinium complexes of such compounds include disodium [[ethylenebis(oxyethylenenitrilo)]tetraaceto]-manganese(II), disodium [[(2-hydroxytrimethylene)dinitrilo]-tetraaceto]manganese(II), sodium [[(2-hyroxytrimethylene)dinitrilo]tetraaceto)gadolinium(III).

5 Claims, No Drawings

METHODS FOR ENHANCING MAGNETIC RESONANCE IMAGING

BACKGROUND OF THE INVENTION

This invention relates to magnetic resonance imaging (MRI), also referred to as nuclear magnetic resonance (NMR) imaging, and more particularly, to methods and compositions for enhancing magnetic resonance images of body organs and tissues.

The recently developed techniques of MRI or NMR imaging encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190–191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g. protons) are irradiated with the appropriate radio-frequency (RF) energy in a highly uniform magnetic field. These nuclei as they relax subsequently emit RF radiation at a sharp resonant frequency. The emitted frequency (RF) of the nuclei depends on the applied magnetic field.

According to known principles, nuclei with appropriate spin when placed in an applied magnetic field [B, expressed generally in units of gauss or tesla ($10^4$ gauss)] align in the direction of the field. In the case of protons, these nuclei precess at a frequency f=42.6 MHz at a field strength of 1 Tesla. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thickness can be selected without loss of resolution. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, x-ray attenuation coefficients alone determine image contrast whereas at least four separate variables ($T_1$, $T_2$, nuclear spin density and flow) may contribute to the NMR signal. For example, it has been shown (Damadian, Science, 171, 1151, 1971) that the values of the $T_1$ and $T_2$ relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physio-chemical changes that may not be detected by x-ray or CT which are only sensitive to differences in the electron density of tissue. The images obtainable by MRI techniques also enable the physician to detect structures smaller than those detectable by CT and thereby provide comparable or better spatial resolution.

Continuing efforts are being made to develop imaging agents for enhancing the images obtained through the use of MRI techniques.

SUMMARY OF THE INVENTION

Among the several objects of the invention may be noted the provision of novel compositions for enhancing magnetic resonance images of body organs and tissues; the provision of such compositions which contain substantially nontoxic manganese or gadolinium complexes of certain tetraacetic acid ligands, and the provision of methods for enhancing magnetic resonance images of body organs and tissues through the administration of such compositions. Other objects and features will be in part apparent and in part pointed out hereinafter.

Briefly, the invention is directed to compositions for enhancing magnetic resonance images of body organs and tissues, the composition comprising a substantially nontoxic manganese or gadolinium complex of a compound of the formula:

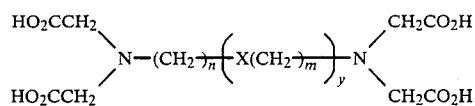

wherein n and m=1, 2, 3 or 4, y=1, 2 or 3, and X is selected from the group consisting of O, S, CHOH and CHSH. The invention is also directed to methods for enhancing magnetic resonance images of body organs and tissues by administering such compositions to a mammal in sufficient amounts to provide enhancement of magnetic resonance images of the body organs and tissues.

DESCRIPTION OF THE PREFERRED EMBODIMENTS

In accordance with the present invention, it has now been found that magnetic resonance images of body organs and tissues may be usefully enhanced through the administration to a mammal of a substantially nontoxic manganese or gadolinium complex of a compound of the formula:

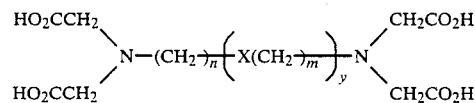

wherein n and m=1, 2, 3 or 4, y=1, 2 or 3 and X is selected from the group consisting of O, S, CHOH and CHSH.

Both manganese and gadolinium are paramagnetic elements capable of altering or enhancing magnetic resonance images, e.e. they are capable of altering the magnetic resonance signal characteristics of body tissues, organs or fluids and thus aid in differentiating normal from diseased tissue. Administered as free ionic salts (e.g. chlorides), they may also exhibit some target organ specificity (e.g. liver). However, such paramagnetic salts or compounds may undesirably exhibit significant toxicity.

It has been found, in accordance with the present invention, that manganese or gadolinium complexes of the above-noted ligands are relatively or substantially nontoxic and are therefore useful for enhancing magnetic resonance images by favorably altering relaxation times $T_1$ and $T_2$ and thereby affording improved contrast between normal and diseased tissue or organs. The complexes of the invention are complexes of manganese or gadolinium and an alkali metal such as sodium or potassium with the aforementioned ligands, the resulting complexes involving a multicoordinate tie-up of the manganese or gadolinium and alkali metal ions. In the above-noted formula, where X is O, the ligand contains an ether linkage between the four carboxylic acid groups, where X is S, the ligand contains a thioether linkage between the four carboxylic acid groups, where X is CHOH, the ligand contains a hydroxymethine linkage between the four carboxylic acid groups and where X is CHSH, the ligand contains a mercaptomethine linkage between the four carboxylic acid groups.

Illustrative manganese and gadolinium complexes of the above-noted class of ligands which may be used in carrying out the invention include disodium [[ethylenebis(oxyethylenenitrilo)]tetraaceto]manganese(II), disodium [[(2-hydroxytrimethylene)dinitrilo]tetraaceto]manganese(II), sodium [[(2-hydroxytrimethylene)dinitrilo]tetraacetato]gadolinium(III), disodium [[trimethylenebis(thioethylenenitrilo)]tetraaceto]manganese(II), sodium [[ethylenebis(oxypropylenenitrilo)]tetraaceto]gadolinium(III), sodium [[(2-mercaptotrimethylene)dinitrilo]tetraacetato]gadolinium(III), and disodium [[2-hydroxytetramethylene)dinitrilo]tetraacetato]manganese(II). Complexes of compounds of the aforementioned formula wherein n and m=1 or 2 and y=1 are preferred. The complexes of the invention may be in the form of hydrates.

As shown by the toxicity studies set forth hereinafter, a representative member of the class of complexes herein contemplated, namely, sodium [[(2-hydroxytrimethylene)dinitrilo]tetraacetato]gadolinium(III), possesses a favorable intravenous toxicity profile. Further, another member of the class, namely, disodium [ethylenebis(oxyethylenenitrilo)]tetraaceto]manganese(II) dramatically reduces $T_1$ and $T_2$ relaxation times of the kidney, liver, spleen, pancreas and gastrointestinal tract.

The substantially nontoxic manganese and gadolinium complexes of the present invention are administered to a mammal in a sufficient amount to provide enhancement of magnetic resonance images of body organs and tissues prior to obtaining a magnetic resonance scan or scans of such organs and tissues with "slices" being taken at the level of the desired organ at various time periods post-administration.

The following examples illustrate the practice of the invention.

EXAMPLE 1

Preparation of Disodium [[(2-Hydroxytrimethylene)dinitrilo]tetraacetato]manganese(II) Hydrate In a 3 L round-bottom flask equipped with a mechanical stirrer was added manganese chloride (64.20 g) and deionized water (600 mL). To the flask was added a solution of sodium hydroxide (40.07 g) and [(2-hydroxytrimethylene)dinitrilo]tetraacetic acid (161.16 g) in 400 mL volume. The reaction mixture which was initially a beige-pink solution became a pink suspension approximately 10 minutes after the reactants were combined. The reaction was treated with $NaHCO_3$ to effect the formation of the disodium salt, and the pH adjusted from approximately 2.5 to 6. The resultant brown solution was filtered, the product precipitated out with ethyl alcohol (3.6 L) and the solids collected by filtration. The solids were air dried over the weekend. The solid (236 g) was dissolved in water (1 L) and recrystallized from ethyl alcohol, dried overnight in a forced air oven at 60° C. and weighed 138.2 g.

The results of elemental analysis were as follows: calculated for $Na_2[Mn(C_{11}H_{14}N_2O_9)]\cdot 1.5H_2O$: C, 29.60; H, 3.83; N, 6.28; Na, 10.30; Mn, 12.31. Found: C, 9.58; H, 3.73; N, 6.26; Na, 10.18; Mn, 12.34.

The solubility of the complex as the hydrate in water was determined to be approximately 40% w/v. The relaxation parameter $T_1$ of a $10^{-3}$M solution of the complex in a 90 MHz NMR experiment was determined to be $0.59\pm0.001$ sec.

EXAMPLE 2

Preparation of Disodium [[Ethylenebis(oxyethylene-nitrilo)]tetraaceto]manganese(II) Hydrate A 2 L 3-neck, round-bottom flask was fitted with a mechanical stirrer, thermometer and nitrogen inlet. To the reaction flask was added water (205 mL), [ethylenebis(oxyethylenenitrilo)]tetraacetic acid (190.20 g), manganese carbonate (57.47 g) and an additional amount of water (250 mL). The reaction was heated to 70°–75° C. and kept at 70°–75° C. for two hours under nitrogen. The suspension cooled to room temperature and was stirred over the weekend. The tan thick suspension was diluted with deionized water (100 mL) and to the suspension was added $NaHCO_3$ (84.01 g). The pH was 7 and the reaction mixture was filtered and treated with washed activated carbon (10 g). The carbon was filtered off and the solution had air drawn across it at room temperature to reduce the volume of solvent. The product precipitated out and was collected in a Buchner funnel on #4 Whatman paper. The material air dried overnight (160 g). The solid (pale yellow-off white in color) was dried in a forced air oven at 60° C. for six hours. The material weighed 140 g. The material was redissolved in water, filtered through a 0.45 Millipore filter and recrystallized.

The results of elemental analysis were as follows: calculated for $C_{14}H_{20}N_2O_{10}MnNa_2\cdot 5H_1O$: C, 29.64; H, 5.33; N, 4.94; Mn, 9.68; Na, 8.10. Found: C, 29.48; H, 5.45; N, 4.86; Mn, 9.74; Na, 8.10.

The solubility of the complex as the hydrate in water was determined to be 100% w/v. The relaxation parameters $T_1$ and $T_2$ of a $10^{-3}$M solution of the complex in a 90 MHz NMR experiment were determined to be 0.16 sec. and 0.50 sec., respectively.

EXAMPLE 3

Preparation of Sodium [[(2-Hydroxytrimethylene)dinitrilo]tetraacetato]gadolinium(III)

A mixture of [(2-hydroxytrimethylene)dinitrilo]tetraacetic acid (8.057 g, 0.025 mol) and sodium hydroxide (1.00 g, 0.025 mol) in water (200 mL) was heated to reflux. Gadolinium oxide (4.531 g, 0.0125 mol) was added and water (50 mL) was used to complete the transfer. The mixture was heated at 80° C. for one hour during which time the solution became homogeneous. Heating at 60° C. was continued overnight. The solvent was removed under reduced pressure to give the solid complex which was formulated as follows:

Excess ligand (15%) was added as the calcium salt (from ligand, 1.208 g and calcium hydroxide, 0.278 g). The material was then taken up in water for injection (20 mL) and the pH was adjusted to 7.0 with 10% sodium hydroxide. The volume of the solution was adjusted to 50 mL with water for injection and the solution was passed through a 0.2μ Millipore filter.

The free metal content of the formulation was found to be <0.01% (weight free metal/weight complex). A $1.0 \times 10^{-3}$M aqueous solution of the complex had $T_1$ and $T_2$ values of 257 msec and 132 msec, respectively.

EXAMPLE 4

Acute Intravenous Toxicity Determination of Disodium [[(2-Hydroxytrimethylene)dinitrilo]tetraacetomanganese(II)

A solution (30% w/v; 0.67 M) of disodium [[(2-hydroxytrimethylene)dinitrilo]tetraaceto)manganese(II) was used.

Male and female Swiss CF-1 albino mice with a body weight range of 17.5 to 29.8 g were employed. The mice were housed according to standard operating procedures and individually marked with picric acid.

The dose schedule was as follows:

| Dose (mmol metal/kg) | Concentration (mmol metal/mL) | Number of Mice Male | Female |
| --- | --- | --- | --- |
| 4.0 | 0.67 | 1 | 1 |
| 2.0 | 0.112 | 1 | 1 |
| 4.0 | 0.112 | 1 | 1 |
| 2.0 | 0.335 | 2 | 2 |
| 3.0 | 0.335 | 2 | 2 |
| 4.0 | 0.335 | 2 | 2 |

Measured single doses were injected into the lateral tail vein at a rate of 1 mL/min. The animals were observed immediately after dosing and during the 7-day post-dosing observation period for pharmacotoxic reactions. Recording of terminal body weights and general necropsy of the thoracic and abdominal organs was performed after 7 days.

The LD$_{50}$ for disodium [[(2-hydroxytrimethylene)-dinitrilo]tetraacetato]manganese(II) was determined to be approximately 2.5 mmol/kg. Reactions following dosing included mild to severe hypoactivity and convulsions. The latter preceded death in almost all instances. Necropsies did not reveal any abnormalities. Weight gains were normal.

EXAMPLE 5

Acute Intravenous Toxicity Determination of Disodium [[Ethylenebis(oxyethylenenitrilo)]tetraaceto]manganese(II)

A solution (40% w/v, 0.84M) of disodium [[ethylenebis(oxyethylenenitrilo)]tetraaceto]manganese(II) was used.

A total of 17 Swiss CF-1 albino mice (9 male, 18.4 g; 8 female, 20.4–20.88 g) were employed for the study. The mice were housed according to standard operating procedures and individually marked with picric acid.

Groups of 1-4 mice, with sexes equally represented, received single intravenous doses of disodium [[ethylenebis(oxyethylenenitrilo)]tetraaceto]manganese(II) according to the following schedule.

| Solution Concentration* | | Intravenous Dose | | Number and Sex of Mice | |
| --- | --- | --- | --- | --- | --- |
| % w/v | M | g/kg | mmol/kg | Male | Female |
| 2 | 0.042 | 0.250 | 0.5 | 2 | 2 |
| 2 | 0.042 | 0.375 | 0.75 | 2 | 2 |
| 2 | 0.042 | 0.425 | 0.85 | 2 | 2 |
| 10 | 0.21 | 0.5 | 1.0 | 1 | — |
| 10 | 0.21 | 1.0 | 2.0 | 1 | 1 |
| 40 | 0.84 | 4.0 | 8.0 | 1 | 1 |

*Dilutions of the 40% solutions were made with Abbott, 0.9% Sodium Chloride for Injection, U.S.P.

The animals were observed immediately after dosing and during the 7-day observation period for pharmacotoxic reactions. Recording of terminal body weights and general necropsy of the thoracic and abdominal organs was performed after 7 days.

The LD$_{50}$ for disodium [[ethylenebis(oxyethylenenitrilo)]tetraaceto]manganese(II) was determined to be approximately 0.75 mmol/kg (0.375 g/kg) which renders its use in MRI dependent on the minimum doses required or on the use of very low doses. Moderate-to-severe convulsions were observed with all the treated animals. All deaths occurred within one minute after dosing. The surviving mice appeared normal within 5 minutes after treatment. Body weight gains were normal after the seven-day observation period and necropsy showed no abnormalities.

EXAMPLE 6

Acute Intravenous Toxicity Determination of Sodium [[(2-Hydroxytrimethylene)dinitrilo]tetraaceto]-gadolinium(III)

A solution (0.68 M with 15% excess ligand as the calcium salt) of sodium [[(2-hydroxytrimethylene)dinitrilo]tetraaceto]gadolinium(III) was used.

Male and female CF-1, SQC strain, albino mice (males, 18.5 to 26.8 g in weight; females, 17.4 to 21.6 g in weight) were used. The mice were housed according to standard operating procedures and individually marked with picric acid.

The mice (2 to 4 per dose level) with sexes equally represented received single intravenous injections at dose levels of 6.8, 10.2 and 13.6 mmol/kg via a lateral tail vein at 1.0 ml/min. The mice were observed immediately after dosing and during the 7-day observation period for pharmacotoxic reactions.

The LD$_{50}$ for sodium [[(2-hydroxytrimethylene)dinitrilo]tetraaceto]gadolinium(III) was determined to be approximately 10.2 mmol/kg as calculated using a modified Behrens-Reed-Muench method (Drug Chem. Toxicol. 4;297–305, 1981).

Immediate deaths occurred at doses of 10.2 (2 out of 4 mice) and 13.6 (4 out of 4 mice) mmol/kg and were preceded by convulsions. In surviving mice, mild hypoactivity was noted up to 0.5 hours in the 10.2 mmol/kg group while no toxic reactions were noted during any time in those mice injected with 6.8 mmol/kg. All surviving mice appeared normal by one hour post-injection. No delayed deaths occurred. Weight gains were normal, and no abnormalities were observed at necropsy of surviving mice.

EXAMPLE 7

Effect of Disodium [[Ethylenebis(oxyethylenenitrilo)]tetraaceto]manganese(II) on Tissue Proton $T_1$ and $T_2$ Relaxation Times Disodium [[ethylenebis(oxyethylenenitrilo)]tetraaceto]manganese(II) as an 0.84 M solution containing 5% molar excess of calcium disodium [ethylenebis(oxyethylonenitrilo)]tetraacetic acid (0.042 M) was used in the study. Two rats (one fasted-time period unknown, 410 g; one non-fasted, 290 g) received 5 mL of the complex orally (4.2 mmol of the complex/rat; 10 mmol/kg and 14 mmol/kg, respectively). The rats were killed 30 minutes after injection and tissue $T_1$ and $T_2$ proton relaxation times were determined using 5 and 10 mHz RADX proton spin analyzers. The results are summarized in the following Table 1:

and 10 mHz frequencies, of the kidney, liver, spleen, pancreas and gastrointestinal tract.

In addition, one non-fasted rabbit received 10 mL of the complex orally (8.4 mmol or 3.8 mmol/kg) and was killed 4 hours after dosing. Tissue $T_1$ and $T_2$ relaxation times were determined at 5 and 10 mHz. The results determined using the 10 mHz RADX proton spin analyzer are shown in the following Table 2:

TABLE 2

Tissue $T_1$ and $T_2$ Relaxation Times 4 hours after Oral Administration of 10 mL of Complex to Rabbit[a]

| Tissue | Untreated Control $T_1$ | $T_1$ 4 Hr. After Complex | Untreated Control $T_2$ | $T_2$ 4 Hr. After Complex |
|---|---|---|---|---|
| Heart | 410 | 220 | 57 | 48 |
| Lung | 484 | 402 | 91 | 96 |
| Fat | 139 | 88 | 125 | 103 |
| Skeletal Muscle | 352 | 379 | 38 | 37 |
| Renal Cortex | 275 | 167 | 69 | 54 |
| Renal Medulla | 546 | 530 | 121 | 118 |
| Liver | 205 | 72 | 52 | 34 |
| Spleen | 337 | 389 | 74 | 64 |
| Pancreas | 205 | 162 | 70 | 66 |
| Bladder | 439 | 250 | 72 | 89 |
| Stomach | 284 | 91 | 56 | 22 |
| Small Intestine | 286 | 33 | 64 | 24 |
| Large Intestine | 284 | 135 | 63 | 37 |

[a]Tissue $T_1$ and $T_2$ relaxation times were determined using a 10 mHz RADX proton spin analyzer and are expressed in msec. Control values were derived from the mean of 18 untreated rabbits. The dose of complex was 3.8 mmol/kg.

Heart, fat, renal cortex, liver and gastrointestinal tract

TABLE 1

Tissue Proton $T_1$ and $T_2$ Relaxation Times (msec) Determined 30 minutes After Oral Administration of 5.0 ml of Complex to Rats

| | 5mHz RADX Determinations | | | | | |
|---|---|---|---|---|---|---|
| Tissue | Untreated Control | 10 mmol Complex/kg | 14 mmol Complex/kg | Untreated Control/kg | 10 mmol Complex/kg | 14 mmol Complex/kg |
| Heart | 434 | 159 | 294 | 29 | 27 | 31 |
| Lung | 482 | 332 | 425 | 53 | 49 | 47 |
| Fat | 179 | 162 | 158 | 101 | 101 | 97 |
| Skeletal Muscle | 405 | 372 | 362 | 32 | 11 | 24 |
| Renal Cortex | 343 | 37 | 99 | — | — | 21 |
| Renal Medulla | — | — | 97 | — | — | 21 |
| Liver | 251 | 17 | 31 | 29 | 7 | 10 |
| Spleen | 398 | 91 | 316 | 45 | 24 | 33 |
| Pancreas | 228 | 22 | 77 | 24 | 8 | 24 |
| Bladder | 453 | 107 | 226 | 30 | 43 | 54 |
| Stomach | 280 | 13 | 13 | 31 | 3 | — |
| Small Intestine | 418 | — | 10 | 40 | — | — |

| | 10mHz RADX Determinations | | | | | |
|---|---|---|---|---|---|---|
| Tissue | Untreated Control | 10 mmol Complex/kg | 14 mmol Complex/kg | Untreated Control/kg | 10 mmol Complex/kg | 14 mmol Complex/kg |
| Large Intestine | 353 | 37 | 42 | 41 | 14 | 14 |
| Heart | 417 | 137 | 341 | 47 | 39 | 47 |
| Lung | 410 | 299 | 385 | 76 | 77 | 75 |
| Fat | 166 | 172 | 160 | 150 | 146 | 157 |
| Skeletal Muscle | 375 | 407 | 399 | 41 | 39 | 33 |
| Renal Cortex | 381 | 36 | 88 | 50 | 19 | 35 |
| Renal Medulla | — | — | 90 | — | — | 36 |
| Liver | 227 | 16 | 29 | 44 | 11 | 16 |
| Spleen | 406 | 82 | 312 | 62 | 30 | 54 |
| Pancreas | 213 | 22 | 78 | 35 | 15 | 42 |
| Bladder | 405 | 128 | 199 | 48 | 51 | 71 |
| Stomach | 240 | 73 | 23 | 46 | 11 | 9 |
| Small Intestine | 396 | 62 | 21 | 70 | 2 | 29 |
| Large Intestine | 367 | 41 | 31 | 59 | 20 | 19 |

[a]Control values represent values determined for one untreated rat using 5 and 10 mHz RADX proton spin analyzers.

Although the data is limited to 2 rats and control values are derived from one rat, the results indicate that oral administration of disodium [[ethylenebis(oxyethylenenitrilo)]tetraaceto]manganese(II) dramatically decreased $T_1$ and $T_2$ relaxation times, as determined at both the 5 $T_1$ values were substantially reduced compared to untreated control values. In addition, $T_2$ values for the gastrointestinal tract were reduced. Thus, disodium [[ethylenebis(oxyethylenenitrilo)]tetraaceto]manganese(II) appears to have potential as an oral agent for MRI enhancement of the liver, pancreas and gastrointestinal tract.

EXAMPLE 8

The complex of Example 1 was administered intravenously to Sprague Dawley rats and New Zealand white rabbits. It was found that the tissue spin lattice relaxation time ($I_1$) of the major target organ, the liver, was reduced up to 80%. Tissue $T_1$ of the heart, pancreas and kidney was also significantly reduced.

Magnetic resonance proton images obtained with the use of a General Electric 0.12T resistive unit or General Electric 1.4T superconducting unit demonstrated enhancement of the liver, heart and kidney following intravenous administration of the complex of Example 1.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A method for enhancing magnetic resonance images of body organs and tissues which comprises administering to a mammal a composition comprising a substantially nontoxic manganese or gadolinium complex of a compound of the formula:

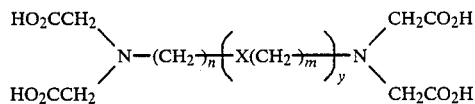

wherein n and m=1, 2, 3 or 4, y=1, 2 or 3 and X is selected from the group consisting of O, S, CHOH and CHSH, in a sufficient amount to provide enhancement of magnetic resonance images of body organs and tissues.

2. A method for enhancing magnetic resonance images of body organs and tissues as set forth in claim 1 wherein said complex is disodium [[ethylenebis(oxyethylenenitrilo)]tetraaceto]manganese(II).

3. A method for enhancing magnetic resonance images of body organs and tissues as set forth in claim 1 wherein said complex is disodium [[(2-hydroxytrimethylene)dinitrilo]tetraaceto]manganese(II).

4. A method for enhancing magnetic resonance images of body organs and tissues as set forth in claim, 1 wherein said complex is sodium [[(2-hydroxytrimethylene)dinitrilo]tetraaceto]gadolinium(III).

5. A method for enhancing magnetic resonance images of body organs and tissues as set forth in claim 1 wherein magnetic resonance images of the hepatobiliary system are enhanced.

* * * * *